United States Patent
Nakamura

(10) Patent No.: US 8,546,997 B2
(45) Date of Patent: Oct. 1, 2013

(54) ULTRASONIC SENSOR

(75) Inventor: Tomoaki Nakamura, Chino (JP)

(73) Assignee: Seiko Epson Corporation, Tokyo (JP)

( * ) Notice: Subject to any disclaimer, the term of this patent is extended or adjusted under 35 U.S.C. 154(b) by 258 days.

(21) Appl. No.: 13/049,221

(22) Filed: Mar. 16, 2011

(65) Prior Publication Data

US 2011/0227449 A1     Sep. 22, 2011

(30) Foreign Application Priority Data

Mar. 19, 2010  (JP) .................................. 2010-063902
Dec. 24, 2010  (JP) .................................. 2010-287179

(51) Int. Cl.
*H01L 41/113*       (2006.01)

(52) U.S. Cl.
CPC ................................... *H01L 41/1138* (2013.01)
USPC ....................................................... 310/322

(58) Field of Classification Search
CPC .......................... H01L 41/1132; H01L 41/1138
USPC ................. 310/322, 334, 338, 339, 340, 344, 310/348
See application file for complete search history.

(56) References Cited

U.S. PATENT DOCUMENTS

| 2002/0053857 A1* | 5/2002 | Scott et al. ..................... 310/314 |
| 2006/0043843 A1* | 3/2006 | Sugiura et al. ................. 310/348 |
| 2010/0148627 A1 | 6/2010 | Funasaka et al. |

FOREIGN PATENT DOCUMENTS

| JP | 2009-025179 A | 6/2009 |
| JP | 2010-165341 A | 7/2010 |
| JP | 2010-183437 A | 8/2010 |
| JP | 2010-210283 A | 9/2010 |

* cited by examiner

*Primary Examiner* — Derek Rosenau

(74) *Attorney, Agent, or Firm* — Global IP Counselors, LLP

(57) ABSTRACT

An ultrasonic sensor includes a support body having an opening, a support film closing the opening, a piezoelectric body disposed on the support film in an inner region of the opening in a plan view, a first resin material forming a first space closed off from an outside space between the first resin material and the support film in at least a region in which the opening is formed in the plan view and the first resin material having an contacting portion facing the opening and being configured to contact with a test object, a second resin material forming a second space closed off from the outside space and communicating with the first space, and an ultrasonic wave transmitting medium filling the first and second spaces. A flexible portion having lower rigidity than the support film in the film thickness direction is provided in a portion of the second resin material.

5 Claims, 12 Drawing Sheets

ULTRASONIC SENSOR

CROSS-REFERENCE TO RELATED APPLICATIONS

This application claims priority to Japanese Patent Application No. 2010-063902 filed on Mar. 19, 2010, and Japanese Patent Application No. 2010-287179 filed on Dec. 24, 2010. The entire disclosures of Japanese Patent Application Nos. 2010-063902 and 2010-287179 are hereby incorporated herein by reference.

BACKGROUND

1. Technical Field

The present invention relates to an ultrasonic sensor, and more specifically to an ultrasonic sensor for sending and receiving ultrasonic waves in the human body.

2. Related Art

As is well known, ultrasonic sensors determine the position and condition of a test object using ultrasonic transducers that send and receive ultrasonic waves (e.g., see Japanese Laid-open Patent Publication No. 2009-25179).

A liquid detecting unit (ultrasonic sensor) disclosed in Japanese Laid-open Patent Publication No. 2009-25179 includes an ultrasonic output unit having an ultrasonic transducer, and an acoustic impedance matching layer disposed on the ultrasonic output unit. In the liquid detecting unit, an ultrasonic transceiving face is formed on one side of the ultrasonic output unit. Also, the acoustic impedance matching layer is formed on one side of the ultrasonic output unit. An output face for outputting ultrasonic waves is formed in the side opposite the side in contact with the ultrasonic output unit. A fluid binder holding recess is formed in the output face. When the output face of the liquid detecting unit is brought into contact with a container, the fluid binder holding recess is filled with a fluid binder as the output face is brought into contact with the container.

A tube-shaped recess-forming member is disposed on one side of the ultrasonic output unit, and the interior of the recess-forming member is filled with an acoustic impedance layer to form a fluid binder holding recess. When the output face is brought into contact with a container, the fluid binder holding recess is filled with fluid binder.

SUMMARY

When a physical condition is detected using the ultrasonic transducer, the output face of the liquid unit described in Japanese Laid-open Patent Publication No. 2009-25179 is brought into contact with a body, and ultrasonic waves are sent and received. In order to detect the physical condition properly, the output face is preferably brought close to the body.

However, in Japanese Laid-open Patent Publication No. 2009-25179 described above, a fluid binder holding recess is formed in the output face. This fluid binder holding recess is filled with a fluid binder, and brought into contact with the body. When fluid binder flows out of the fluid binder holding recess under these conditions, it can make contact with the body and the output face. Also, bubbles can form between the body and the output face. The ultrasonic waves are reflected by the bubbles, and the detection process cannot be performed properly. A configuration in which the output face is flat and free of a recess has been considered. Here, the output face is pressed against the body. However, while the body and the output face come into contact, internal deflection occurs on the output face, and the ultrasonic transceiving face of the ultrasonic transducer disposed adjacent to the acoustic impedance layer is also deformed.

A configuration has also been considered in which a tube-shaped recess-forming member is formed on the side of the ultrasonic output unit in which the ultrasonic transceiving face is disposed. Here, the output face is formed in the end portion of the recess-forming member, and the interior of the recess-forming member is sealed. Also, the acoustic impedance layer for the liquid is disposed on the inside of the sealed recess-forming member. However, when the output face is brought into contact with a body, the deflection of the output face increases the internal pressure on the acoustic impedance layer of the liquid, and the internal pressure deforms the acoustic transceiving face.

When the acoustic transducer is deformed in this way, the amount of displacement of the ultrasonic transceiving face by the vibration is reduced, and ultrasonic waves cannot be sent and received properly.

An object of the present invention is to provide an ultrasonic sensor able to send and receive ultrasonic waves properly.

An ultrasonic sensor according to a first aspect of the present invention includes a support body, a support film, a piezoelectric body, a first resin material, a second resin material, and an ultrasonic wave transmitting medium. The support body has an opening. The support film is disposed on the support body and covering the opening. The piezoelectric body is disposed on an inner region of the opening in a plan view seen in a thickness direction of the support film, the piezoelectric body being formed by laminating a lower electrode, a piezoelectric film, and an upper electrode in this order on the support film. The first resin material forms a first space closed off from an outside space, the first space being formed by the first resin material and the support film in at least a region in which the opening is formed as seen in the plan view, the first resin material having an contacting portion facing the opening, and configured to contact with a test object. The second resin material forms a second space communicating with the first space, the second space being closed off from the outside space, at least a portion of the second resin material including a flexible portion having lower rigidity than the support film in the film thickness direction. The ultrasonic wave transmitting medium fills the first space and the second space.

In the first aspect, the first space is formed at least between the first resin material and the region of the support film closing off the opening, and the first space is filled with an ultrasonic wave transmitting medium. This ultrasonic wave transmitting medium can be water or saline, which effectively transmit ultrasonic waves. This medium can properly transmit ultrasonic waves without attenuation. Also, an contacting portion is provided in the region of the first resin material opposite the opening. By bringing the test object into contact with the contacting portion, the ultrasonic waves generated by the vibrating support film can be transmitted to the test object, and the ultrasonic waves reflected by the test object can be transmitted to the support film.

Here, as mentioned above, when the test object is brought into contact with the contacting portion of the first resin material, the contacting portion experiences deflection, and the pressure inside the first space increases. However, in the present invention, a second space communicating with the first space is provided by a second resin material, and a flexible portion that is less rigid than the support film is disposed in the second resin material. Thus, when the pressure inside the first space increases, the flexible portion bulges towards the outside space, and the ultrasonic wave transmitting medium inside the first space flows into the second space.

Therefore, even when the test object is brought into contact with the contacting portion, and the pressure inside the first space increases, deformation of the support film can be restrained. In other words, when voltage is applied to a piezoelectric body, and the support film is vibrated, or when ultrasonic waves are received by the support film and vibrated, the vibration of the support film is not attenuated, and ultrasonic waves are sent and received properly.

In the ultrasonic sensor as described above, preferably, the support film covers one side of the support body, the first resin material has a first recessed portion opening towards the support film with the first space being formed by connecting an open end of the first recessed portion to the support film, the second resin material has a second recessed portion opening towards the support film with the second space being formed by connecting an open end of the second recessed portion to the support film, and the first resin material and the second resin material are integrally formed.

Because the first resin material and the second resin material are integrally formed in the present invention, the same resin material can be used, and manufacturing costs can be decreased. Also, the first space and the second space can be easily formed when the first recess in the first resin material and the open end of the second recess in the second resin material are closed off by the support film. As a result, the manufacturing process can be simplified.

In the ultrasonic sensor as described above, preferably, the opening in the support body passes through the support body in the thickness direction, the support film covers one side of the support body, the first resin material has a first recessed portion opening towards the support film with the first space being formed by connecting an open end of the first recessed portion to another side of the support body opposite from the one side, and the second resin material has a second recessed portion opening towards the support film with the second space being formed by connecting an open end of the second recessed portion to the another side of the support body.

However, when the open ends of the recesses are connected to the support film covering one side of the support body, and the test object is firmly brought into contact with the contacting portion of the first resin material opposite the opening in the support body, the contacting portion may come into contact with the support film, and with the piezoelectric body disposed in the support film. This may cause the support film and the piezoelectric body to rupture. In this aspect, the open ends of the first recess in the first resin material and the second recess in the second resin material are connected to the other side of the support body not covered by the support film. Therefore, the first space is increased inside the first recess, and includes the inside region with the opening. When the test object is firmly brought into contact with the contacting portion of the first resin material and pressure from the contacting portion increases the deflection on the support film side, the contacting portion comes into contact with the support body. In other words, the contacting portion does not come into contact with the support film and the piezoelectric body, and the support film and the piezoelectric body are prevented from rupturing.

Preferably, the ultrasonic sensor as described above further includes a displacement detecting section configured to detect displacement of the flexible portion, and an ultrasonic wave transmitting section configured to execute one of a voltage-applying process for applying a voltage to the piezoelectric body and a detection process for detecting a signal outputted from the piezoelectric body, when displacement of the flexible portion is detected by the displacement detecting section.

This aspect also includes a displacement detecting section for detecting displacement of the flexible portion. Therefore, when displacement of the flexible portion of the second resin material is detected by the displacement detecting section, contact between the test object and the contacting portion can be detected. As a result, the voltage application process for transmitting ultrasonic waves from the ultrasonic wave transmitting section is executed after contact with the test object has been detected by the displacement detecting section. In this way, the ultrasonic waves reliably reach the test object.

Preferably, the ultrasonic sensor as described above further includes a determining section configured to determine whether an amount of displacement of the flexible portion detected by the displacement detecting section is within a range of a predetermined threshold value. The ultrasonic wave transmitting section is preferably configured to execute one of the voltage-applying process and the detection process when the determining section has determined that the amount of displacement in the flexible portion is within the range of the predetermined threshold value.

However, when the test object is firmly brought into contact with the contacting portion of the first resin material, the support film on which the piezoelectric body is disposed may experience significant deflection. In this situation, even when ultrasonic waves have been transmitted to the test object, the ultrasonic waves reflected by the test object may not be transmitted properly, and the detection process may not be performed properly. When determining means determines whether or not the amount of displacement is within the range of a predetermined threshold value, the ultrasonic wave transmitting section executes either the voltage application process in which ultrasonic waves are transmitted, or the detection process.

In other words, when the amount of displacement falls outside of the range for a predetermined threshold value, the ultrasonic wave transmitting section does not execute the voltage application process or detection process. The voltage application process can be executed, and the detection process can be executed properly only when the amount of displacement falls within the range of a predetermined threshold value.

BRIEF DESCRIPTION OF THE DRAWINGS

Referring now to the attached drawings which form a part of this original disclosure.

DETAILED DESCRIPTION OF EXEMPLARY EMBODIMENTS

First Embodiment

Figure 1:
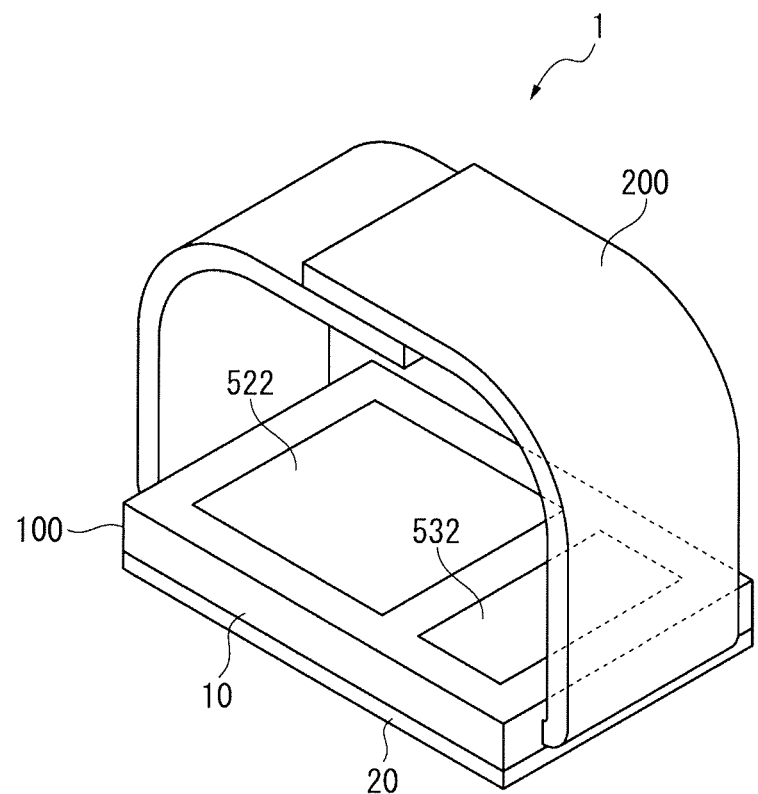
FIG. 1 is an outline view showing the appearance of the biological testing device according to a first embodiment of the present invention.
Figure 2:
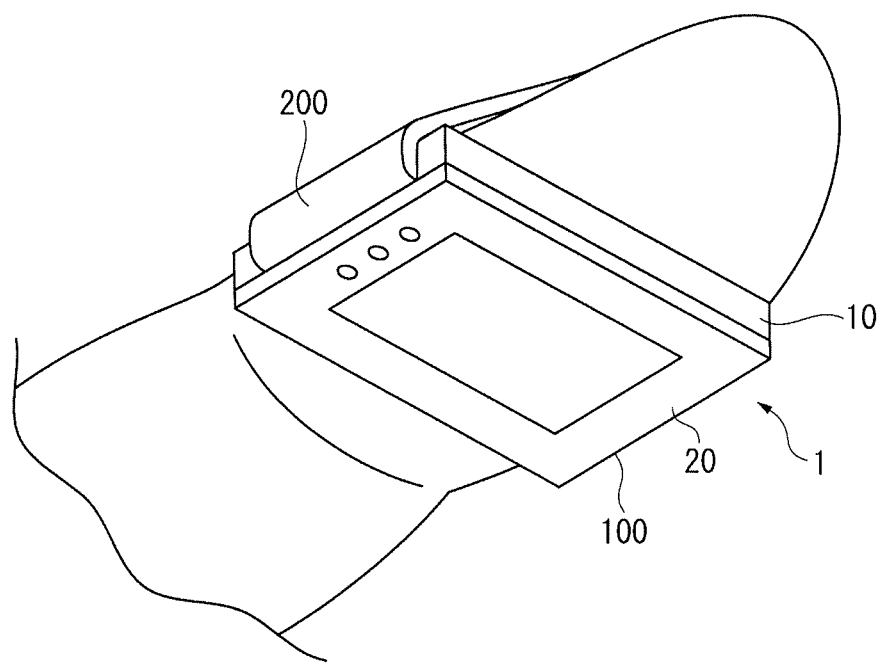
FIG. 2 is a view showing how the biological testing device in the first embodiment is attached to the human body.
Figure 3:
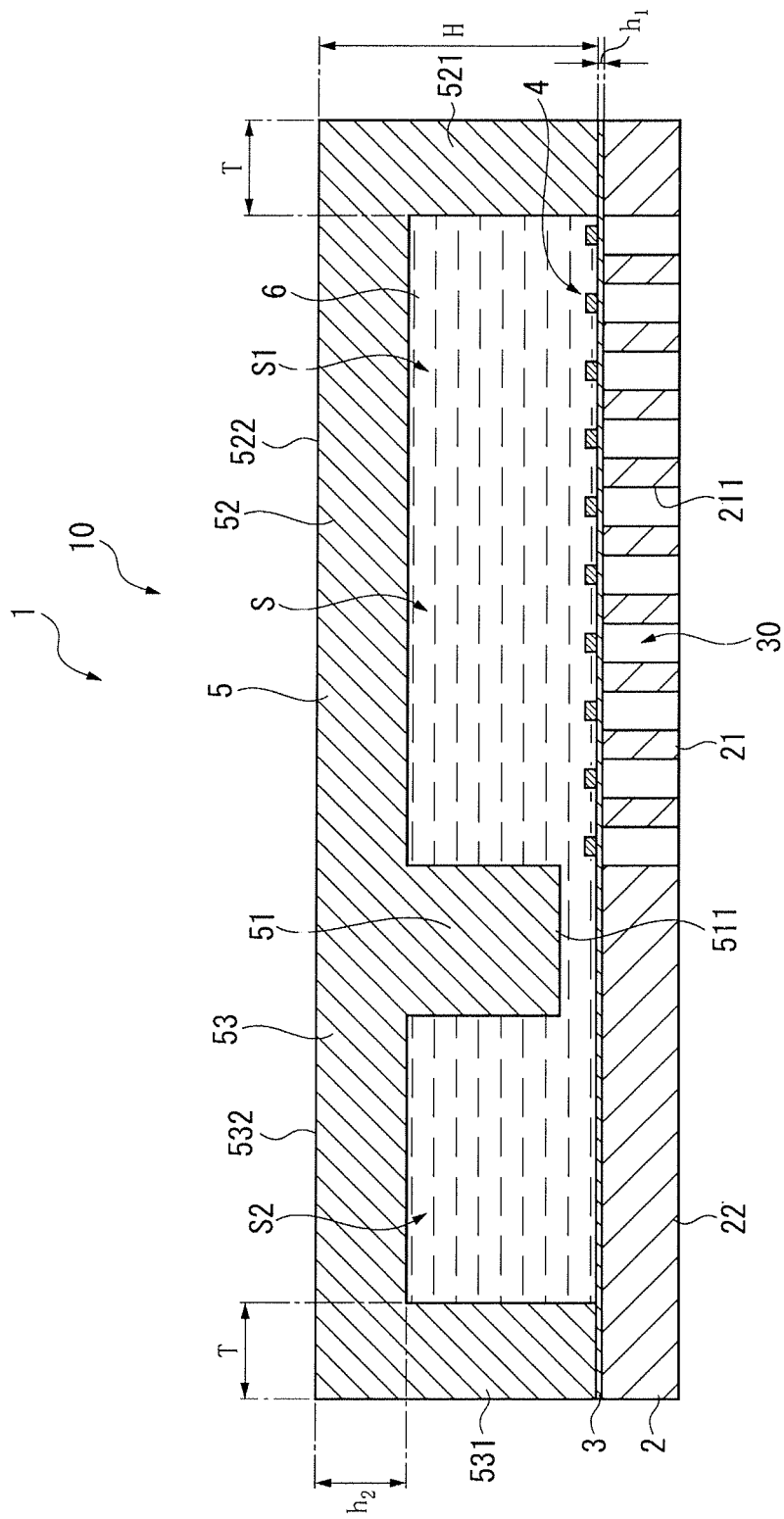
FIG. 3 is a cross-sectional view schematically illustrating the biological testing device in the first embodiment.

The following is a description of the first embodiment of the present invention, made with reference to the accompanying drawings. FIG. 1 is an outline view showing the appearance of the biological testing device 1 according to a first embodiment of the present invention, which is an ultrasonic sensor. FIG. 2 is a view showing how the biological testing device 1 in the first embodiment is attached to a human finger. FIG. 3 is a cross-sectional view schematically illustrating the ultrasonic transceiver 10 incorporated into the biological testing device 1. For illustrative purposes, the band 200 has been omitted in FIG. 3.

Configuration of Biological Testing Device

As shown in FIG. 1 and FIG. 2, the biological testing device 1 in this embodiment is attached to a finger using a band 200. This biological testing device 1 includes a main unit 100, and a band 200 for attaching the main unit 100 to a finger. The main unit 100 includes an ultrasonic transceiver 10, a control unit (not shown) for controlling the ultrasonic transceiver 10 and executing the biological testing, and a front panel 20 having input buttons for operating the biological testing device 1 and a display panel for displaying the test results. When ultrasonic waves are transmitted to the finger by the biological testing device 1, ultrasonic waves reflected by a biological structure such as the blood vessels in the finger are received, the blood flow is tested using, for example, pulse and blood pressure, and other physiological conditions are tested. In the explanation of this embodiment, the biological testing device 1 is a device attached to a human finger. However, the present invention is not restricted in this way. For example, it can be attached to other body parts such as a wrist, ankle, or toe. A securing attachment such as a band 200 does not have to be used. The tester can simply press the ultrasonic transceiver 10 against the body, and test internal conditions or prenatal conditions using ultrasonic waves. Also, the test object does not have to be the human body, and the device can be used to detect the interior or surface of a test object using ultrasonic waves.

When the biological testing device 1 is attached to a finger, the ultrasonic transceiver 10 is disposed on the side making contact with the finger. As shown in FIG. 1 and explained below, the device is equipped with a contact portion 522 serving as the contacting portion, and a flexible portion 532. Because the main unit 100 is forcibly brought into contact with the finger by the band 200, the tester does not have to apply pressure to the ultrasonic transceiver 10, and the contact portion 522 comes into ready contact with the finger. Also, ultrasonic waves can be transmitted between the body and the ultrasonic transceiver 10.

The contact unit is connected electrically to the ultrasonic transceiver 10 and various configurational elements of the front panel 20 so that their operation can be controlled. More specifically, the control unit controls the operation of the ultrasonic transceiver 10 by switching between an ultrasonic transmission mode and an ultrasonic reception mode. Ultrasonic waves are transmitted in the ultrasonic transmission mode, and ultrasonic waves are received in the ultrasonic reception mode. Also, in the ultrasonic reception mode, blood flow is measured using pulse and blood pressure based on the detection signals outputted from the ultrasonic transceiver 10. Also, the control unit, for example, starts or stops testing and displays test results on the display panel based on control signals inputted from the input buttons on the front panel 20.

Configuration of Ultrasonic Transceiver

As shown in FIG. 3, the ultrasonic transceiver 10 in the biological testing device 1 includes a sensor array substrate 2 serving as the support body, a support film 3 laminated on the sensor array substrate 2, a plurality of ultrasonic transducers 4 arranged on the support film 3 for sending and receiving ultrasonic waves, a resin material 5 covering the support film 3 to form a space S with the support film 3, and an ultrasonic wave transmitting medium 6 filling the space S. The configuration of the ultrasonic transducers 4 is explained below.

The sensor array substrate 2 has a first support portion 21 forming the region in which the plurality of ultrasonic transducers 4 are arranged, and a second support portion 22 adjacent to the outer peripheral portion of the first support portion 21. These can be formed, for example, from a semiconductor forming material such as single-crystal silicon (Si). Also, openings 211 having a round shape in plan view (sensor plan view), i.e., when the sensor array substrate 2 is viewed from the direction perpendicular to the plane of the sensor array substrate 2, are formed corresponding to the positions in which the ultrasonic transducers 4 are formed, as explained below. The radius (a) of the openings 211 is, for example, 50 μm.

Also, the support film 3 is formed on top of the sensor array substrate 2 to a uniform thickness dimension. In this way, the openings 211 are closed off by the support film 3. The thickness dimension $h_1$ of the support film 3 can be, for example 2 μm. In the following explanation, the region of the support film 3 closing off the openings 211 is referred to as the diaphragm 30. More specifically, the support film 3 is formed with a two-layer structure composed of a $SiO_2$ layer formed on top of the sensor array substrate 2, and a $ZrO_2$ layer formed on top of the $SiO_2$ layer. The support film 3 can be formed, for example, by using heat to oxidize a sensor array substrate 2 made of Si to form the $SiO_2$ layer, and then applying a Zr layer and thermal oxidizing the Zr layer to form the $ZrO_2$ layer. The support film 3 has a two-layer structure composed of a $SiO_2$ layer and a $ZrO_2$ layer, and the following calculations are made in this embodiment so that the two layers in the support film 3 are adjusted, and the Young's modulus of the support film 3 is approximately 70 GPa. Because, as mentioned above, the radius (a) of the openings 211 is 50 μm, the radius (a) of the diaphragm 30 is the same (i.e., 50 μm), and the area is $7.85 \times 10^{-3}$ ($mm^2$). When the flexural rigidity D of the diaphragm 30 is calculated using Equation (1) below, where Poisson's ratio v is 0.3, the result is $5.13 \times 10^{-8}$ (Pa·$m^3$). In this embodiment, the openings 211 have a round shape for good stress balance when the diaphragm 30 is deflected. However, the openings can also be rectangular or oval shaped.

Equation (1)

$$D = \frac{Eh^3}{12(1-v^2)} \quad (1)$$

D: flexural rigidity (Pa·m³), E: Young's modulus (Pa), h: thickness dimension (m), v: Poisson's ratio When the maximum deflection $\omega_{max}$ of the diaphragm 30 used to close the opening 211 was calculated using Equation (2) below based on the flexural rigidity D, the result was $1.9 \times 10^{-12} \times q$ (m)

Equation (2)

$$w_{max} = \frac{qa^4}{64D} \quad (2)$$

$\omega_{max}$: maximum deflection (m), q: load per unit area (Pa), a: opening, radius of flexible portion (m)

The resin material 5 comes into contact with the outer peripheral edge of the support film 3 on the sensor array substrate 2, and surrounds the sensor array substrate 2, forming a space S with the sensor array substrate 2 that is sealed off from the outside space. This space S is filled with an ultrasonic wave transmitting medium 6. This resin material 5 can be formed, for example, using silicone rubber. More specifically, the resin material 5 includes a partitioning portion 51 partitioning the space S into a first space S1 and a second space S2, and forming a communication hole 511 to allow the spaces S1, S2 to communicate, a first resin portion 52 forming the first space S1 on top of the first support portion 21 along with the partitioning portion 51 and the support film 3, and a second resin portion 53 forming the second space S2 on top of the second resin portion 22 along with the partitioning portion 51 and the support film 3.

The first resin portion 52 has a first resin wall portion 521 standing erect along the outer peripheral edge of the first support portion 21 on the sensor array substrate 2, and a contact portion 522 facing one side of the main unit 100 opposite the first support portion 21. Here, the contact portion 522 is formed from the end portion of the support film 3 away from the first resin wall portion 521 to the end portion of the support film 3 away from the partitioning portion 51. In other words, the first resin wall portion 521, the contact portion 522, and the partitioning portion 51 constitute the first resin material of the present invention, and a portion formed by the first resin wall portion 521, the contact portion 522, and the partitioning portion 51 is the first recess of the present invention. Also, the first resin wall portion 521, the contact portion 522, and the partitioning portion 51 form the first space S1 sealed off from the outside space, along with the support film 3 formed on top of the sensor array substrate 2.

The second resin portion 53 has a second resin wall portion 531 standing erect along the outer peripheral edge of the second support portion 22 disposed over the support film 3 outside of the first support portion 21, and a flexible portion 532 facing one side of the main unit 100 opposite the second support portion 21. Here, the flexible portion 532 is formed from the end portion of the support film 3 away from the second resin wall portion 531 to the end portion of the support film 3 away from the partitioning portion 51. In other words, the second resin wall portion 531, the flexible portion 532, and the partitioning portion 51 constitute the second resin material of the present invention, and a portion formed by the second resin wall portion 531, the flexible portion 532, and the partitioning portion 51 is the second recess of the present invention. Also, the second resin wall portion 531, the contact portion 532, and the partitioning portion 51 form the second space S2 sealed off from the outside space, along with the support film 3 formed on top of the sensor array substrate 2.

As mentioned above, the partitioning portion 51 is the portion partitioning the space S into a first space S1 and a second space S2. It is formed along the boundary portion between the first support portion 21 and the second support portion 22 on top of the support film 3 in the sensor plan view. Also, as shown in FIG. 3, the communication whole 511 formed by the partitioning portion 51 is formed between the support film 3 and the partitioning portion 51. However, it can be formed through the partitioning portion 51 as well. As for the number of communication holes 511 formed, a plurality of communication holes 511 can be formed to allow the first space S1 and the second space S2 to communicate. For example, a single long communication hole 511 can be formed in the direction of the wall surface in the partitioning portion 51 (i.e., in the direction perpendicular to the surface of the paper in FIG. 3).

In the resin material 5 mentioned above, the wall thickness dimension T of the first resin wall portion 521 and the second resin wall portion 531 can be, for example 1 mm. The thickness dimension $h_2$ of the contact portion 522 and the flexible portion 532 is also 1 mm. Also, the height dimension H of the resin material 5 covering the support film 3 (i.e., the height dimension H of the first resin wall portion 521, the second resin wall portion 531, and the partitioning portion 51 from the support film 3) is 2 mm. Also, the size of the contact portion 522 is the sensor plan view is 3 mm×3 mm, and the size of the flexible portion 532 is 3 mm×2 mm. In other words, the area of the flexible portion 532 is 6 (mm²). Also, as mentioned above, silicone rubber can be used as the resin material 5. However, the Young's modulus of silicone rubber is approximately $4.0 \times 10^6$ (Pa) under temperature conditions from room temperature to body temperature. When the flexural rigidity D of the flexible portion 532 is calculated using Equation (1) above, where Poisson's Ratio v is 0.5, the result is $4.44 \times 10^{-4}$ (Pa·m³). In this embodiment, the flexible portion 532 has a rectangular shape in the sensor plan view. However, in order to facilitate a comparison of the flexible portion 532 to the diaphragm 30, which is round-shaped in sensor plan view, the flexible portion 532 is assumed to have a round shape with a radius (a) of $1.5 \times 10^{-3}$ (m) based on a flexible portion 532 with an area of 6 (mm²). When the maximum deflection $\omega_{max}$ of the flexible portion 532 is calculated using Equation (1) above based on the flexural rigidity D, the result is $1.78 \times 10^{-10} \times q$ (m). In this embodiment, silicone rubber is used as the resin material 5. However, it is not restricted to this material. Any material with similar properties can be used.

Also, in this embodiment, the volume of the first space S1 is greater than the volume of the second space S2. There is no particular restriction on the volumes of the spaces S1, S2. The volume of the second space S1 can be greater than the volume of the first space S1, or both can have the same volume. In this embodiment, only one second space S2 is formed. However, for example, two second spaces S2 can be formed to interpose the first space S1. They can also be formed around the entire outer periphery of the first space S1.

The ultrasonic transmitting medium 6 is used to more effectively transmit ultrasonic waves. In this embodiment, a liquid having nearly the same acoustic impedance as the human body is used, such as water or saline, because the device is used to test the interior of a human body using ultrasonic waves. Other examples of ultrasonic transmitting media 6 include a high-viscosity carboxyl methylcellulose aqueous solution, castor oil, and liquid paraffin.

Figure 4:
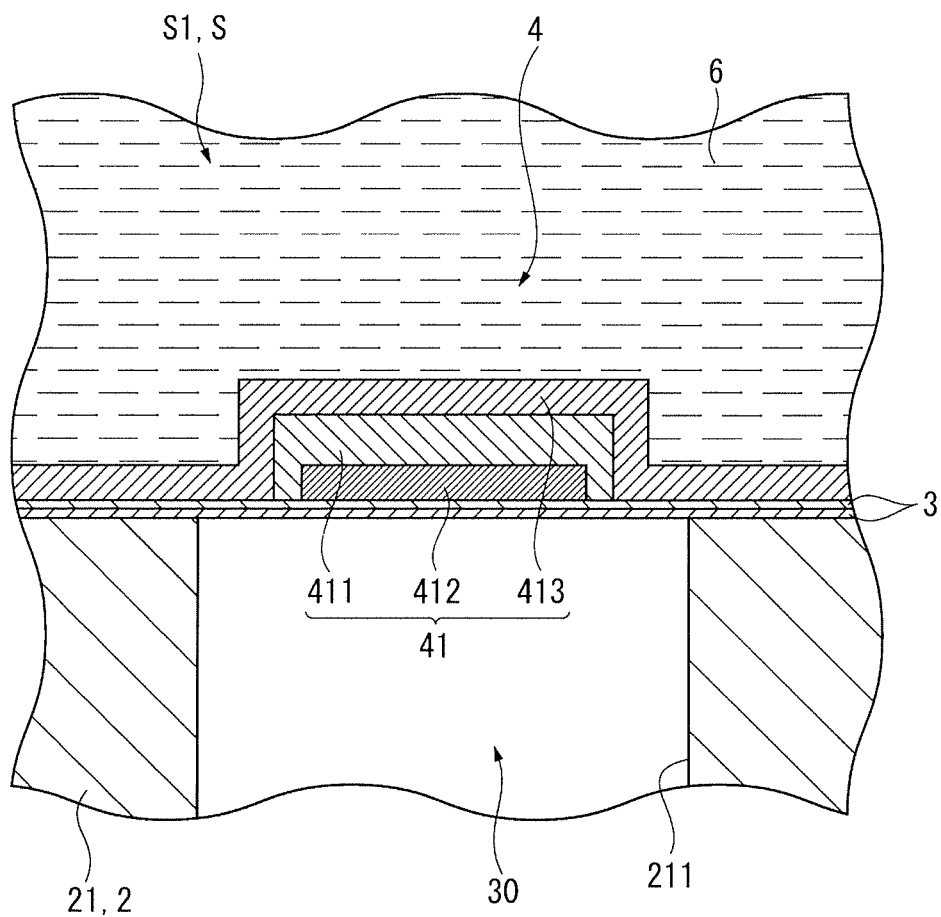
FIG. 4 is a cross-sectional view showing the ultrasonic transducer in the first embodiment.
Figure 5:
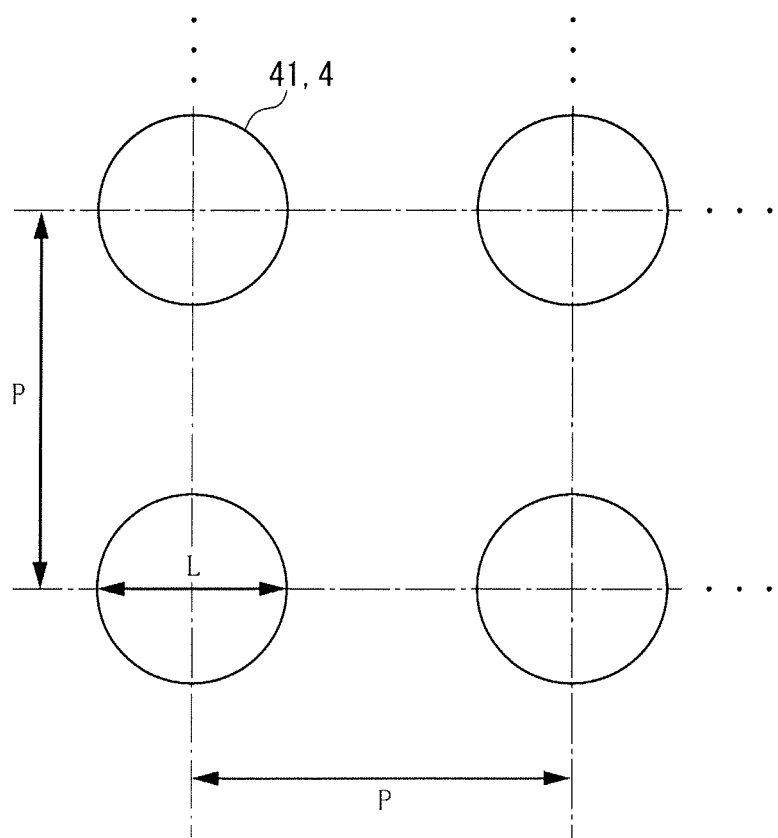
FIG. 5 is a schematic view showing the layout of the ultrasonic transducers in the first embodiment.

FIG. 4 is a cross-sectional view showing an ultrasonic transducer 4. FIG. 5 is a schematic view showing the layout of the ultrasonic transducers 4. An ultrasonic transducer 4 is an element that transmits ultrasonic waves based on signals from the control unit, receives ultrasonic waves, and outputs them to an arithmetic control unit. As shown in FIG. 3, a plurality of ultrasonic transducers 4 are disposed on top of the first support portion 21 of the sensor array substrate 2. For example, ten can be arranged vertically and ten can be arranged horizontally in the sensor plan view, as shown in FIG. 3 and FIG. 5. These ultrasonic transducers 4 have a first support portion 21 on the sensor array substrate 2, a support film 3, and a piezoelectric component 41. As mentioned above, the first support portion 21 is the portion on the sensor array substrate 2 in which the ultrasonic transducers 4 are arranged. Openings 211 are formed in the positions where the ultrasonic transducers 4 are formed. As mentioned above, the support film 3 is formed on top of the sensor array substrate 2, and a diaphragm 30 is formed to close off the openings 211.

The piezoelectric component 41 is a film-shaped component formed on the diaphragm 30 in the center position of the diaphragm 30. The piezoelectric component 41 is formed with a substantially round shape in plan view and has a diameter dimension L of, for example, 80 μm, which is smaller than the diameter dimension of the openings 211 (100 μm). A plurality of piezoelectric components 41 are formed so that the pitch P of the piezoelectric components 41 is 200 μm. A piezoelectric component 41 has a piezoelectric film 411, and electrodes (lower electrode 412 and upper electrode 413) to apply voltage to the piezoelectric film 411.

A piezoelectric film 411 is, for example, lead zirconate titanate (PZT) formed into film. In this embodiment, PZT is used for the piezoelectric film 411. However, any material that shrinks in the planar direction when voltage is applied can be used. Examples include lead titanate ($PbTiO_3$), lead zirconate ($PbZrO_3$), and lead lanthanum titanate ($(Pb, La)TiO_3$). The lower electrode 412 and the upper electrode 413 are formed with the piezoelectric film 411 interposed between them. The upper electrode 413 and the lower electrode 412 are drawn from a drawing portion (not shown) formed on the sides of the openings 211, and are connected to the control unit of the biological testing device 1.

When a predetermined drive voltage is applied from the control unit between the electrodes 412, 413 of the piezoelectric component 41 in an ultrasonic transducer 4, the piezoelectric film 411 expands and contracts in the planar direction. This vibrates the diaphragm 30 in the film thickness direction, and ultrasonic waves at a frequency corresponding to the cycle of the predetermined drive voltage are transmitted from the diaphragm 30 towards the contact portion 522. In other words, the ultrasonic transducer 4 functions as a transmission unit for transmitting ultrasonic waves towards a finger. The ultrasonic transducer 4 also functions as a receiving unit for receiving ultrasonic waves reflected by, for example, the blood vessels inside the finger. At this time, the diaphragm 30 is vibrated by the reflected ultrasonic waves, and electric signals corresponding to their amplitude and frequency are outputted from the piezoelectric component 41 to the control unit via the lower electrode 412 and the upper electrode 413. Here, the control unit switches the mode of the ultrasonic transducer 4 between the ultrasonic transmission mode and the ultrasonic reception mode so that the ultrasonic transducer 4 functions either as a receiving unit or a transmitting unit. In this embodiment, the ultrasonic transducers 4 are combination ultrasonic wave transmitting units and receiving units, and the control unit switches between these functions. However, dedicated ultrasonic wave transmitting transducers can also be combined with dedicated ultrasonic wave receiving transducers. In one example, the transmitting transducers and the receiving transducers can be arranged in alternating fashion on a single array substrate. In another example, a transmission array substrate composed of a plurality of transmitting transducers, and a reception array substrate composed of a plurality of receiving transducers are arranged in separate locations.

Operation of Biological Testing Device

Figure 6:
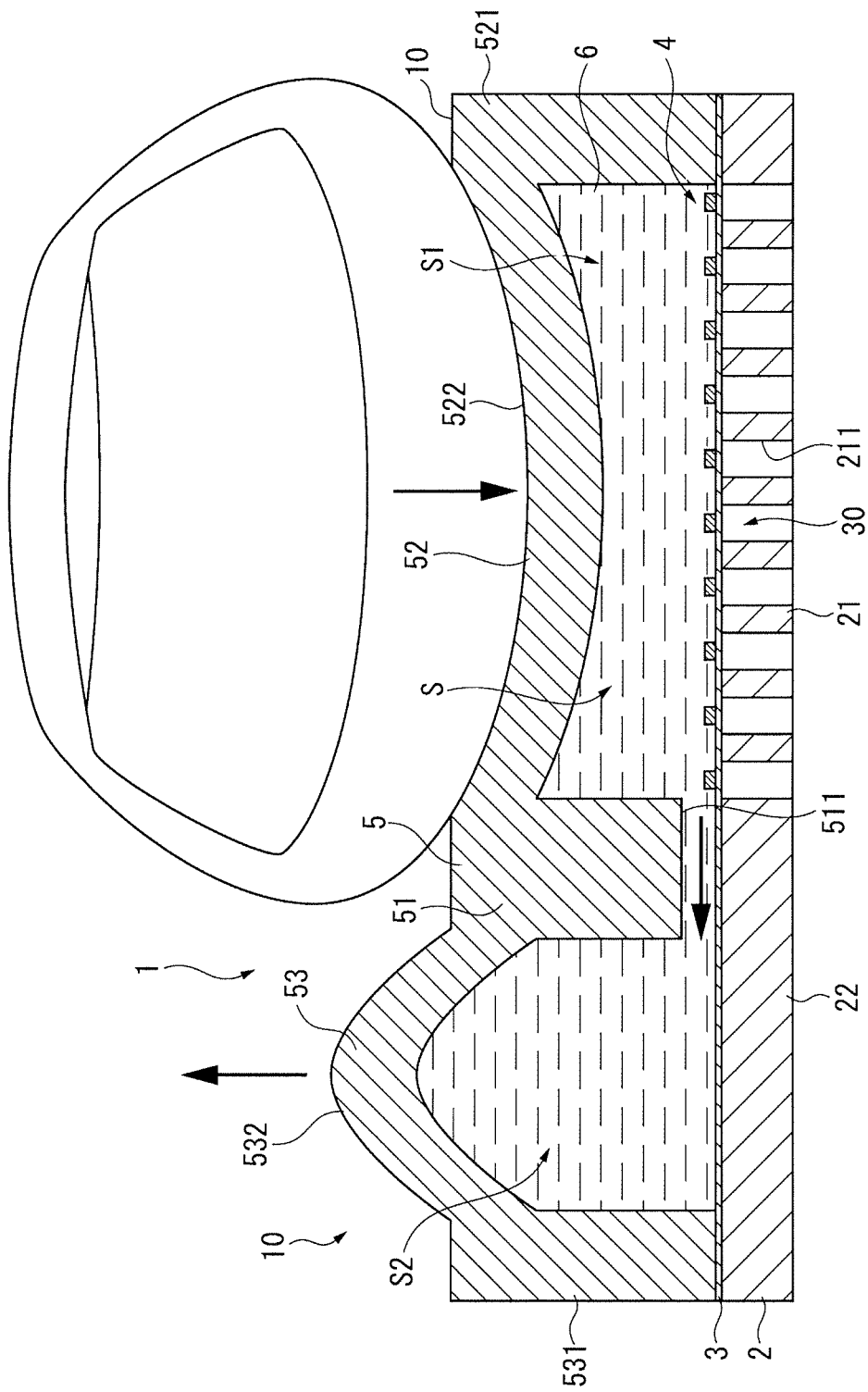
FIG. 6 is a cross-sectional view schematically illustrating the operation of the biological testing device in the first embodiment.

FIG. 6 is a cross-sectional view schematically illustrating the operation of the biological testing device 1. In order to test vascular conditions using this biological testing device 1, the biological testing device 1 is first attached to a finger using the band 200 (see FIG. 1). By adjusting the fastening strength of the band 200, the biological testing device 1 is attached and secured so as to press the contact portion 522 of the biological testing device 1 against the finger. At this time, the amount of deflection in the diaphragm 30 depends on the fastening strength of the band 200. However, the contact portion 522 usually can be brought into contact with the finger at a maximum deflection $\omega_{max}$ for the diaphragm 30 of approximately $1.9 \times 10^{-12} \times q$ (m).

When the biological testing device 1 is attached, the contact portion 522 is facing the support film 3. This reduces the volume of the first space S1, and the pressure inside the first space S1 increases. Here, as mentioned above, the flexural rigidity D of the diaphragm 30 is sufficiently greater than the flexural rigidity D of the flexible portion 532. As a result, the rise in pressure inside the first space S1 causes the ultrasonic wave transmitting medium 6 inside the first space S1 to flow via the communication hole 511 into the second space S2, and the flexible portion 532 having low flexural rigidity D bulges towards the outside space. Because, as mentioned above, the maximum deflection $\omega_{max}$ of the diaphragm 30 is approximately $1.9 \times 10^{-12} \times q$ (m) and the maximum deflection $\omega_{max}$ of the flexible portion 532 is approximately $1.78 \times 10^{-10} \times q$ (m), the flexible portion 532 bulges and the diaphragm 30 experiences no deflection.

For example, when the user operates the input buttons disposed on the front panel 20 (see FIG. 2) and operating signals to start the measurements are inputted to the control unit, the control unit applies a predetermined drive voltage between the electrodes 412, 413 of the piezoelectric component 41. This causes the ultrasonic transducers 4 to transmit ultrasonic waves from the diaphragm 30 towards the finger. These ultrasonic waves are transmitted inside the finger attached to the contact portion 522 via an ultrasonic wave transmitting medium 6 having substantially the same acoustic impedance as the human body and via the contact portion 522. Immediately after the ultrasonic waves have been transmitted, the application of voltage to the electrodes 412, 413 in the ultrasonic transducers 4 is stopped. In other words, the controller switches the ultrasonic transducers 4 from ultrasonic transmission mode to ultrasonic reception mode.

When the ultrasonic waves transmitted from the ultrasonic transducers 4 have been reflected by, for example, the blood vessels inside the finger, they are again propagated from the contact portion 522 through the ultrasonic wave transmitting medium 6, and received by the diaphragm 30. The diaphragm 30 is vibrated based on the intensity of the received ultrasonic waves, and detection signals (electric current) is outputted from the piezoelectric components 41 on the diaphragm 30 to the control unit. Next, the control unit measures blood flow conditions, such as the pulse and blood pressure, based on the inputted detection signals and, for example, displays the detection results on the display panel disposed on the front panel 20.

Operational Effects of First Embodiment

The biological testing device 1 in the first embodiment has the following effects. In this embodiment, a first space S1 is formed by the region of the support film 3 closing off the openings 211 and the first resin material 52, and the first space S1 is filled with an ultrasonic wave transmitting medium 6. Because a liquid is used as the ultrasonic wave transmitting medium 6 having substantially the same acoustic impedance as the acoustic impedance of the human body, ultrasonic waves can be propagated properly without attenuation. Also, because a contact portion 522 is disposed in the first resin portion 52 facing the openings 211, and the contact portion 522 is brought into contact with a finger, the ultrasonic waves generated by the vibrating diaphragm 30 can be transmitted into the finger, and the ultrasonic waves reflected by the blood vessels in the finger can be transmitted to the diaphragm 30. Here, as described above, when the contact portion 522 of the first resin portion 52 is brought into contact with a finger, the contact portion 522 experiences deflection, and the pressure inside the first space S1 increases. However, in this embodiment, a second space S2 communicating with the first space S1 is formed by the second resin portion 53, and a flexible portion 532 having a flexural rigidity D lower than the flexural rigidity D of the diaphragm 30 is disposed in the second resin portion 53. Thus, even when the pressure inside the first space S1 has increased, the flexible portion 532 bulges towards the outside space, and the ultrasonic wave transmitting medium 6 inside the first space S1 flows into the second space S2. Therefore, deformation of the diaphragm 30 can be suppressed even when the contact portion 522 is brought into contact with a finger and the pressure inside the first space S1 increases. Also, the vibration of the diaphragm 30 is not attenuated and ultrasonic waves are sent and received properly when voltage is applied to the piezoelectric component 41 and the diaphragm 30 is vibrated, and when ultrasonic waves are received and the diaphragm 30 is vibrated.

Second Embodiment

Figure 7:
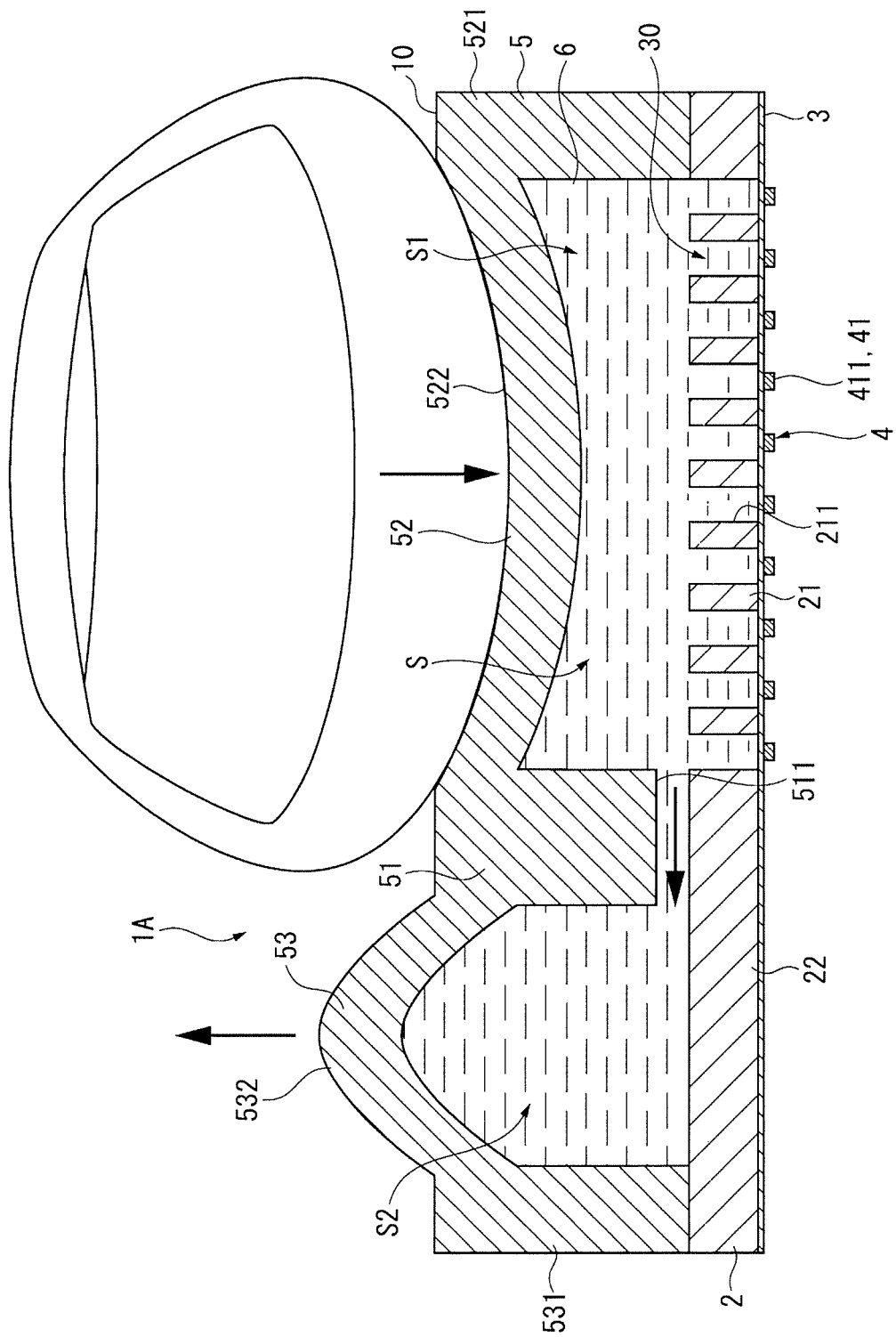
FIG. 7 is a cross-sectional view schematically illustrating the operation of the biological testing device in a second embodiment of the present invention.

The following is an explanation with reference to the drawings of the biological testing device 1A in the second embodiment. FIG. 7 is a cross-sectional view schematically illustrating the operation of the biological testing device 1A in the second embodiment. In the explanation of the drawing, the configurational elements identical to those in the previous embodiment are denoted by the same reference numerals. Further explanation of these elements has been omitted. The same is true of other embodiments explained below. In the biological testing device 1A in the second embodiment, a space S is formed by a sensor array substrate 2 and a resin material 5, and a support substrate 3 is arranged on the sensor array substrate 2 on the outside space side. On these points, this embodiment differs from the first embodiment. In other words, the arrangement of the ultrasonic transducers 4 in the first embodiment has been changed.

In the biological testing device 1A, the support film 3 is arranged on the sensor array substrate 2 on the outside space side, and the piezoelectric component 41 is arranged on the support film 3 on the side opposite the side facing the contact portion 522 of the first resin portion 52. In other words, the piezoelectric component 41 is arranged outside of the first space S1. In this configuration, the opening 211 in the first support portion 21 forms the first space S1, and the opening 211 is filled with an ultrasonic wave transmitting medium 6.

In an ultrasonic transducer 4 of the first embodiment, the ultrasonic waves were transmitted from the surface of the piezoelectric film 411 on the side opposite the side facing the support film 3. However, in an ultrasonic transducer 4 of the present embodiment, the ultrasonic waves are transmitted from the surface of the piezoelectric film 411 on the side facing the support film 3.

Even though, as described above, ultrasonic waves are transmitted from the surface of the piezoelectric film 411 on the side facing the support film 3 in the biological testing device 1A of the second embodiment, the effects are similar to those of the first embodiment. Even when the support portion 522 is firmly brought into contact with a finger, the contact portion 522 is pressed, and significant deflection is experienced on the support film 3 side, the contact portion 522 comes into contact with the first support portion 21 of the sensor array substrate 2. In other words, it does not come into contact with the piezoelectric component 41 or support film 3, and damage to the piezoelectric component 41 and the support film 3 can be prevented.

Modification of the Second Embodiment

Figure 8:
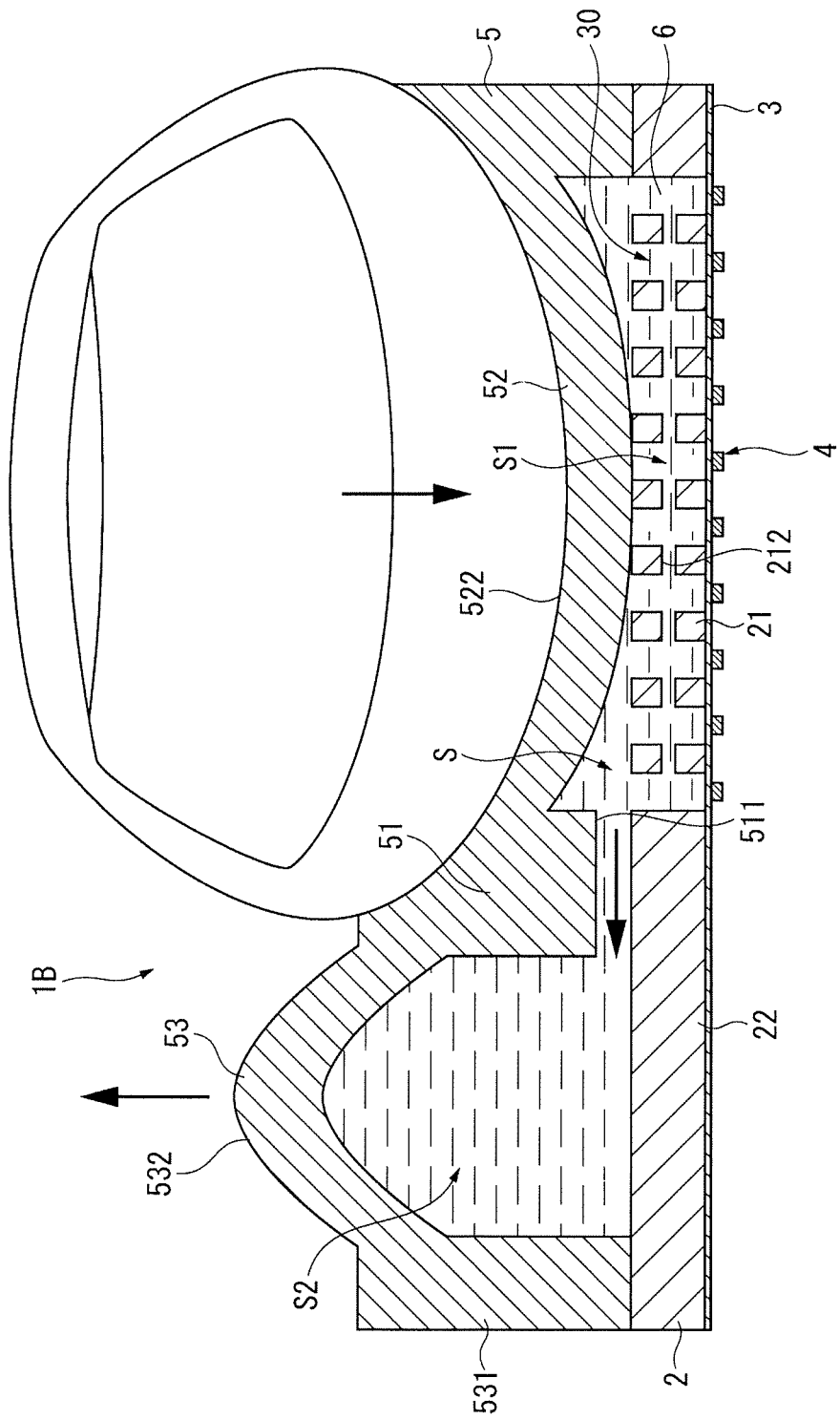
FIG. 8 is a cross-sectional view schematically illustrating the operation of the biological testing device in a modification of the second embodiment.

FIG. 8 is a cross-sectional view schematically illustrating the operation of the biological testing device 1B in a modification of the second embodiment. In this modification, a through-hole 212 passes through the first support portion 21 in the direction perpendicular to the thickness direction of the support film 3.

Here, when the contact portion 522 is firmly pressed against a finger, the contact portion 522 comes into contact with the first support portion 21 as shown in FIG. 8. In the configuration of the second embodiment under this situation, the first space S1 is partitioned by the first resin portion 52, and the ultrasonic wave transmitting medium 6 on the second space S2 side of the first space S1 readily flows into the second space S1, whereas the ultrasonic wave transmitting medium 6 in the first space S1 on the side opposite that of the second space S2 is less likely to flow into the second space S2 because of the first support portion 21. When the contact portion 522 comes into contact with the first support portion 21, the contact portion 522 closes off the opening 211, and the diaphragm 30 experiences deflection because of the rising pressure inside the first space S1.

In the configuration of this modification, a through-hole 212 is formed in the first support portion 21 even when the contact portion 522 comes into contact with the first support portion 21. As a result, the ultrasonic wave transmitting medium 6 on the side of the first space S1 opposite the side with the second space S1 is allowed to flow into the second space S2 via the through-hole 212. Therefore, the effects are similar to those of the other embodiments. When the contact portion 522 comes into contact with the first support portion 21 and the contact portion 522 closes off the opening 211, the diaphragm 30 is prevented from experience deflection due to an increase in pressure inside the first space S1.

Third Embodiment

Figure 9:
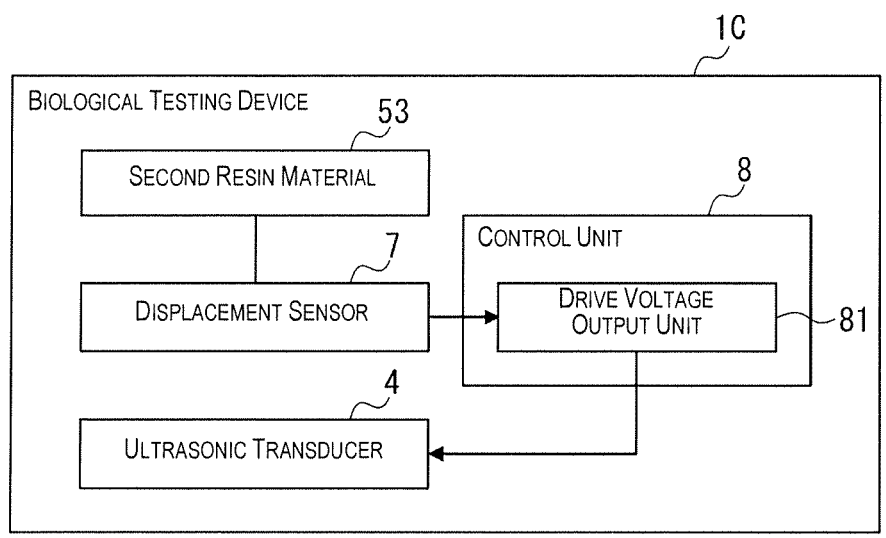
FIG. 9 is a block diagram of the biological testing device in a third embodiment of the present invention.

The following is an explanation with reference to the drawings of the biological testing device 1C in the third embodiment. In the following explanation, both FIG. 3 and FIG. 4 are referenced. FIG. 9 is a block diagram of the biological testing device 1C in the third embodiment. The biological testing device 1C in the third embodiment has a displacement sensor 7 serving as a displacement detecting section for detecting displacement of the second resin material 52, and a control unit 8 for detecting detection signals from the displacement sensor 7 and controlling the biological testing device 1C accordingly. It differs from the other embodiments in this respect.

The displacement sensor 7 detects displacement of the flexible portion 532 in the second resin portion 53. On detecting displacement of the flexible portion 532, the displacement sensor 7 outputs a detection signal to the control unit 8. Here, the displacement sensor 7 can be a contact sensor or a differential transformer. In this case, displacement is detected based on the voltage difference generated in two coils by electromagnetic induction. The present invention is not restricted to a contact sensor. A non-contact sensor can also be used. For example, an electrostatic capacitance sensor can be used in which displacement is detected based on the change in electrostatic capacitance. Displacement can be detected using an ultrasonic transducer based on the ultrasonic wave reflection time. A strain sensing element can also be installed in the flexible portion 532 to detect displacement.

The control unit 8 includes a drive voltage output unit 81 serving as ultrasonic wave transmitting section in which voltage signals are outputted to the electrodes 412, 413 of an ultrasonic transducer 4 (voltage application process), and blood flow conditions such as pulse and blood pressure are measured based on the voltage signals outputted from the piezoelectric component 41 (detection process). When detection signals are inputted from the displacement sensor 7, the drive voltage output unit 81 outputs voltage signals to the electrodes 414, 413 of an ultrasonic transducer 4. When detection signals are not inputted from the displacement sensor 7, the drive voltage output unit 81 detects that the finger has been removed from the contact portion 522, and the outputting of voltage signals to the electrodes 412, 413 is stopped. The drive voltage output unit 81 detects the voltage signals outputted from the piezoelectric component 41 receiving ultrasonic waves, and measures the blood flow conditions such as pulse and blood pressure based on the voltage signals.

First, when a finger comes into contact with the contact portion 522, the contact portion 522 experiences internal deflection, and the ultrasonic wave transmitting medium 6 in the first space S1 flows into the second space S2 via the communication hole 511. The flexible portion 532 composing the second space S2 bulges, and the displacement sensor 7 detects the displacement and outputs a detection signal to the drive voltage output unit 81 of the control unit 8. When detection signals have been inputted from the displacement sensor 7, the drive voltage output unit 81 determines that a finger has come into contact with the contact portion 522. The ultrasonic transducers 4 are switched to ultrasonic transmission mode, and voltage signals are outputted to the electrodes 412, 413 of the ultrasonic transducers 4. Thus, as mentioned above, the electrodes 412, 413 apply a predetermined voltage to the piezoelectric film 411 based on the inputted voltage signals, and ultrasonic waves are transmitted from the diaphragm 30 to the contact portion 522. The drive voltage output unit 81 switches the ultrasonic transducers 4 to ultrasonic wave transmission mode. When ultrasonic waves reflected by the finger in contact with the contact portion 522 are received by the diaphragm 30, voltage signals are outputted to the drive voltage output unit 81 of the control unit 8, and the drive voltage output unit 81 measures the blood flow conditions such as pulse and blood pressure based on the voltage signals.

In addition to the effects of the first embodiment, the biological testing device 1C in the third embodiment has the following effect. In this embodiment, the control unit 8 determines that a finger has come into contact with the contact portion 522, and the drive voltage output unit 81 of the control unit 8 outputs voltage signals to the electrodes 412, 413. As a result, ultrasonic waves are reliably transmitted and ultrasonic waves reliably reach a finger only when a finger has come into contact with the contact portion 522.

Fourth Embodiment

Figure 10:
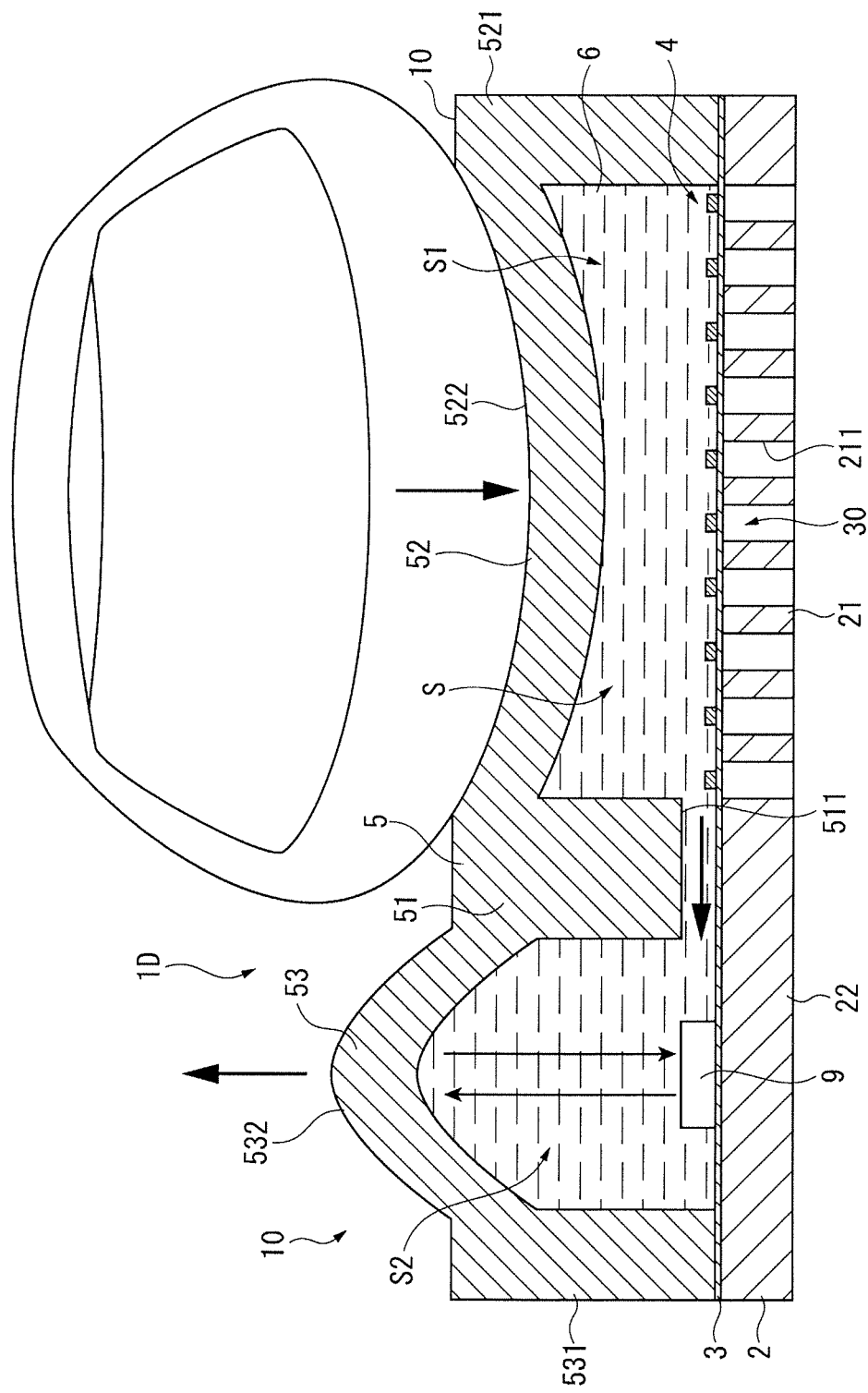
FIG. 10 is a cross-sectional view schematically illustrating the operation of the biological testing device in a fourth embodiment of the present invention.
Figure 11:
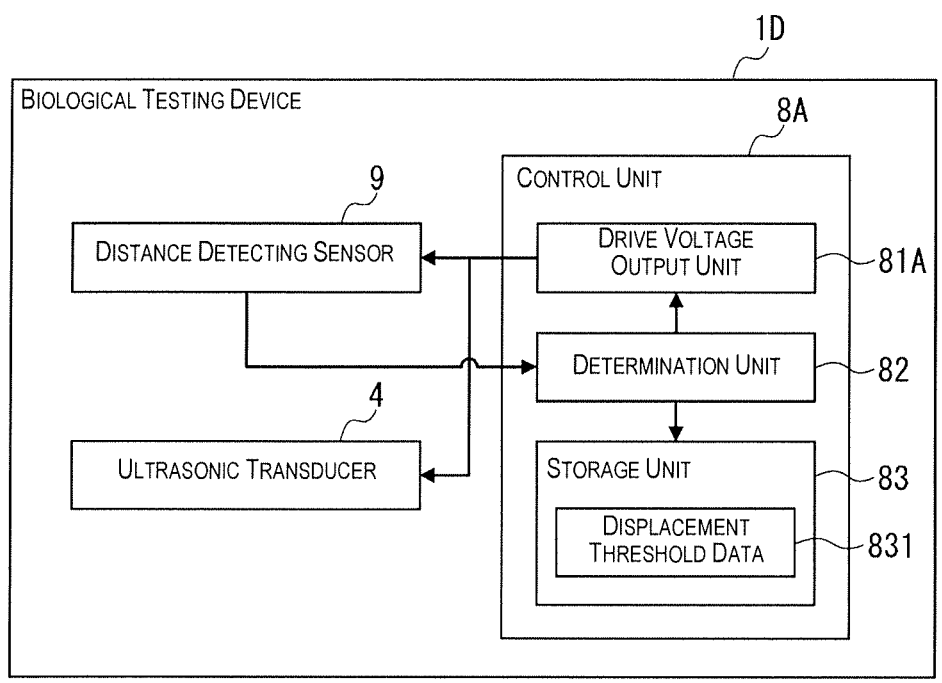
FIG. 11 is a block diagram of the biological testing device in a fourth embodiment of the present invention.

The following is an explanation of the biological testing device 1D in the fourth embodiment with reference to FIG. 10 and FIG. 11. The biological testing device 1D of the fourth embodiment has a distance detecting sensor 9 serving as the displacement detecting section for detecting the amount of displacement in the flexible portion 532 of the second resin portion 53, and a control unit 8A for detecting detection signals from the distance detecting sensor 9 and controlling the biological testing device 1D accordingly. It is different from the other embodiments in this respect. More specifically, in the third embodiment, when the displacement sensor 7 detects that the flexible portion 532 of the second resin portion 53 has been displaced, the control unit 8 switches the ultrasonic transducers 4 to the ultrasonic wave transmission mode. However, in this embodiment, the distance detecting sensor 9 measures the amount of deflection (amount of displacement) in the flexible portion 532 of the second resin portion 53. The control unit 8 then switches the ultrasonic transducers 4 to the ultrasonic wave transmission mode based on the amount of deflection.

The distance detecting sensor 9 detects the amount of deflection in the flexible portion 532 of the second resin portion 53. When the distance detecting sensor 9 has detected the amount of deflection in the flexible portion 532, detection signals are outputted to the control unit 8A. Here, the distance detecting sensor 9 detects the amount of deflection in the flexible portion 532 using the ultrasonic transducers based on the ultrasonic wave reflection time. As shown in FIG. 10, the sensor is disposed on the second support portion 22 of the support film 3. Instead of using the ultrasonic transducers, the distance detecting sensor 9 can be an electrostatic capacitance sensor that detects the amount of deflection based on the change in electrostatic capacitance. The plurality of ultrasonic transducers 4 arranged on the first support portion 21 can also be disposed on the second support portion 22 as the distance detecting sensor 9. Here, the openings 211 formed in the first support portion 21 are formed in the second support portion 22, and the region of the support film 3 closing off the openings 211 serves as the diaphragm 30. Ultrasonic transducers 4 are then arranged above the diaphragm 30. In this configuration, the first support portion 21 and the second support portion 22 are identical, and ultrasonic transducers 4 can be disposed above the diaphragm 30. As a result, the distance detecting sensor 9 can be disposed on the second support portion 22 at the same time the ultrasonic transducers 4 are disposed on the first support portion 21. This simplifies the manufacturing process.

The control unit 8A has a drive voltage output unit 81A, a determination unit 82 (determining section), and a storage unit 83. The storage unit 83 is composed of a recording medium such as a memory unit or a hard disk. It stores in a readable format the displacement threshold value data 831

(predetermined threshold) and program needed in the process executed by the determination unit 82. The displacement threshold value data 831 is data on the amount of deflection (amount of displacement) experienced by the flexible portion 532 of the second resin portion 53 when a finger has come into contact with the contact portion 522 of the first resin portion 52 that does not affect the support film 3.

When input buttons on the front panel 20 (see FIG. 2) have been operated, the drive voltage output unit 81A outputs voltage signals to the distance detecting sensor 9. The drive voltage output unit 81A also outputs voltage signals to the electrodes 412, 413 of the ultrasonic transducers 4 based on the determination signals from the determination unit 82 (voltage application process). In addition, the drive voltage output unit 81A detects the voltage signals outputted from piezoelectric components 41 that have received ultrasonic waves, and measures blood flow conditions such as pulse and blood pressure based on the voltage signals (detection process).

When output signals have been inputted from the distance detecting sensor 9, the determination unit 82 retrieves displacement threshold value data 831 from the storage unit 83, and compares the displacement threshold value data to the amount of displacement in the flexible portion 532. When the determination unit 82 has determined that the amount of deflection in the flexible portion 532 is within the range of the displacement threshold value data 831, determination signals are outputted to the drive voltage output unit 81A. When the determination unit 82 has determined that the amount of deflection in the flexible portion 532 is outside of the range of the displacement threshold value data 831, a notice to adjust the finger is displayed on the display panel in the front panel 20 (see FIG. 2).

Figure 12:
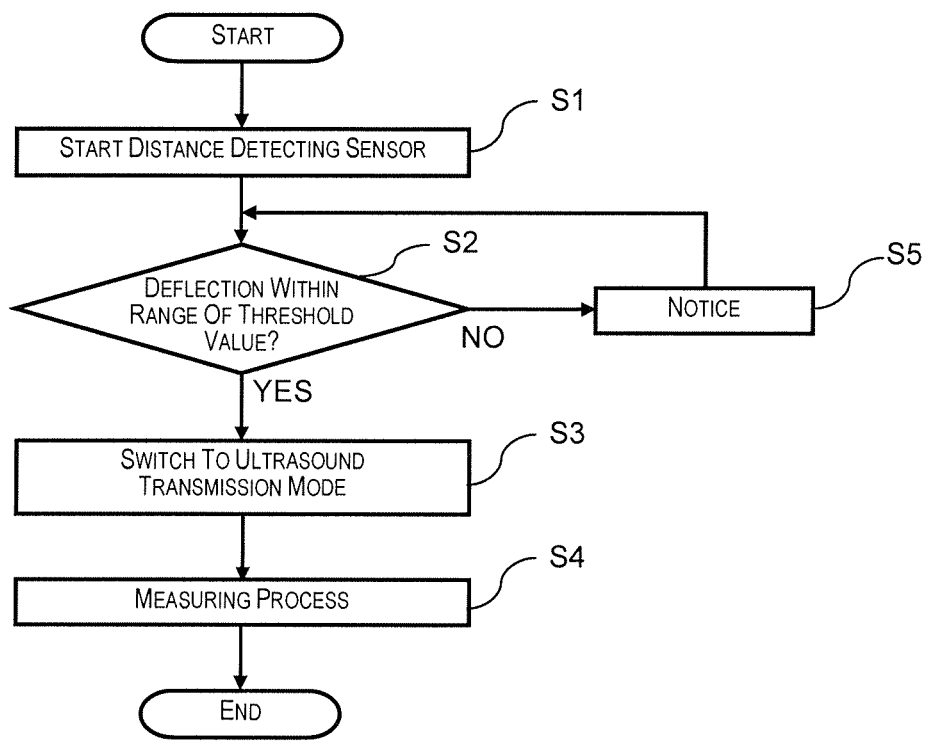
FIG. 12 is a flowchart for the biological testing device in the fourth embodiment of the present invention.

The following is an explanation of the operations performed by the biological testing device 1D in the fourth embodiment with reference to the flowchart in FIG. 12. First, when the input buttons on the front panel 20 (see FIG. 2) have been operated, the drive voltage output unit 81A starts the distance detecting sensor 9 (Step S1). Next, when detection signals have been inputted from the distance detecting sensor 9, the determination unit 82 compares the displacement threshold value data 831 to the amount of deflection experienced by the flexible portion 532 (Step S2). When the amount of deflection experienced by the flexible portion 532 has been determined to be within the range of the displacement threshold value data 831 in the comparison, the drive voltage output unit 81A switches the ultrasonic transducers 4 to the ultrasonic wave transmission mode, and outputs voltage signals to the electrodes 412, 413 of the ultrasonic transducers 4 (Step S3). The drive voltage output unit 81A then switches the ultrasonic transducers 4 to the ultrasonic wave reception mode, and measures the blood flow conditions such as pulse and blood pressure based on the voltage signals inputted from the piezoelectric components 41 (Step S4). When the amount of deflection experienced by the flexible portion 532 has been determined to be outside of the range of the displacement threshold value data 831 in the comparison, the determination unit 82 displays a notice to adjust the finger on the display panel (Step S5).

In addition to the effects of the first embodiment, the biological testing device 1D in the fourth embodiment has the following effect.

According to this embodiment, the distance measuring sensor 9 detects the amount of deflection experienced by the flexible portion 532, and the determination unit 82 compares the amount of deflection to the displacement threshold value data 831. When the amount of deflection experienced by the flexible portion 532 falls outside of the range of the displacement threshold value data 831, a notice is displayed indicating that the finger has to be pressed more firmly against the flexible portion 532. In this situation, the drive voltage output unit 81A does not perform the voltage application process in which ultrasonic waves are transmitted. Therefore, when the amount of deflection experienced by the flexible portion 532 falls outside of the range of the displacement threshold value data 831, the drive voltage output unit 81A does not perform the voltage application process and the detection process. The voltage application process can only be executed and the detection process can only be executed properly when the amount of deflection is within the range of the displacement threshold value data 831.

Modification of Embodiments

The present invention is not limited to the embodiments described above. The present invention includes any modification or improvement within a scope allowing the object of the present invention to be achieved.

In these embodiments, the space S is partitioned into a first space S1 and a second space $S_2$ by a partitioning portion 51. However, a partitioning portion 51 does not have to be used. In this case, when a finger is brought into contact with the contact portion 522 and the contact portion 522 experiences internal deflection, the ultrasonic wave transmitting medium 6 can flow into the space S and the flexible portion 532 bulges.

In these embodiments, the first resin portion 52 and the second resin portion 53 are made of the same material and have the same thickness dimensions h2, T. However, they can be made of different materials and can have different thickness dimensions. Also, the flexible portion 532 alone can be made of a different material and have a different thickness dimension. Also, the flexible portion 532 can have a round shape in the sensor plan view.

In the embodiments, the flexible portion 532 is formed opposite the second support portion 22. However, it can also be formed on the side with the second resin portion 53.

In the embodiments, the size of the contact portion 522 in the first resin portion 52 is 3 mm×3 mm, relative to a plan view of the sensor. However, the present invention is not limited to this arrangement; the size of the contact portion 522 can be determined by the shape and size of the test object making contact therewith.

In the embodiments, a communication hole 511 is disposed for communication between the first space S1 and the second space S2. However, the first space S1 and the second space S2 can also communicate via a cylindrically shaped member such as a tube. In this case, the second space S2 is configured solely using the second resin portion 53, which is formed in the shape of a pouch, and the second resin portion 53 does not need to be secured to the support film 3 and the sensor array substrate 2.

In the embodiments, the second space S2 is formed on the second support portion 22. However, the present invention is not limited to this arrangement. For example, it can be disposed on the side surface of the main unit 100, and the flexible portion 532 exposed on the side surface of the main unit 100. The flexible portion 532 can also be exposed in a portion of the front panel 20 on the main unit 100. This would allow the amount of displacement in the flexible portion 532 to be confirmed visually in order to determine whether the finger was in contact with the contact portion 522. In this embodiment, the support film 3 is arranged on top of the sensor array substrate 2. However, it can also be arranged only in those places closing off the openings 211 in the first support portion 21. In the embodiments, the openings 211 pass through the sensor array substrate 2. However, the present invention is not limited to this arrangement. Recesses can also be used. Here, the support film 3 would close off the openings in the recesses. A support film 3 can also be formed on the bottom surface of the recesses.

General Interpretation of Terms

In understanding the scope of the present invention, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" or "element" when used in the singular can have the dual meaning of a single part or a plurality of parts. Finally, terms of degree such as "substantially", "about" and "approximately" as used herein mean a reasonable amount of deviation of the modified term such that the end result is not significantly changed. For example, these terms can be construed as including a deviation of at least ±5% of the modified term if this deviation would not negate the meaning of the word it modifies.

While only selected embodiments have been chosen to illustrate the present invention, it will be apparent to those skilled in the art from this disclosure that various changes and modifications can be made herein without departing from the scope of the invention as defined in the appended claims. Furthermore, the foregoing descriptions of the embodiments according to the present invention are provided for illustration only, and not for the purpose of limiting the invention as defined by the appended claims and their equivalents.

What is claimed is:

1. An ultrasonic sensor comprising:
   a substrate having an opening therein;
   a support film disposed on the substrate and covering the opening;
   a piezoelectric body disposed on an inner region of the opening in a plan view seen in a thickness direction of the support film, the piezoelectric body being formed by laminating a lower electrode, a piezoelectric film, and an upper electrode in this order on the support film, the piezoelectric body having a width that is smaller than that of the opening in a direction perpendicular to the thickness direction;
   a first resin material forming a first space closed off from an outside space, the first space being formed by the first resin material and the support film in at least a region in which the opening is formed as seen in the plan view, the first resin material having an contacting portion overlapping the opening, and configured to contact with a test object;
   a second resin material forming a second space communicating with the first space, the second space being closed off from the outside space, at least a portion of the second resin material including a flexible portion having lower rigidity than the support film in the film thickness direction, the flexible portion being configured to bulge toward the outside space; and
   an ultrasonic wave transmitting medium filling the first space and the second space.

2. The ultrasonic sensor of claim 1, wherein
   the support film covers one side of the support body,
   the first resin material has a first recessed portion opening towards the support film with the first space being formed by connecting an open end of the first recessed portion to the support film,
   the second resin material has a second recessed portion opening towards the support film with the second space being formed by connecting an open end of the second recessed portion to the support film, and
   the first resin material and the second resin material are integrally formed.

3. The ultrasonic sensor of claim 1, wherein
   the opening in the support body passes through the support body in the thickness direction,
   the support film covers one side of the support body,
   the first resin material has a first recessed portion opening towards the support film with the first space being formed by connecting an open end of the first recessed portion to another side of the support body opposite from the one side, and
   the second resin material has a second recessed portion opening towards the support film with the second space being formed by connecting an open end of the second recessed portion to the another side of the support body.

4. The ultrasonic sensor of claim 1, further comprising
   a displacement detecting section configured to detect displacement of the flexible portion, and
   an ultrasonic wave transmitting section configured to execute one of a voltage-applying process for applying a voltage to the piezoelectric body and a detection process for detecting a signal outputted from the piezoelectric body, when displacement of the flexible portion is detected by the displacement detecting section.

5. The ultrasonic sensor of claim 4, further comprising
   a determining section configured to determine whether an amount of displacement of the flexible portion detected by the displacement detecting section is within a range of a predetermined threshold value, and
   the ultrasonic wave transmitting section is configured to execute one of the voltage-applying process and the detection process when the determining section has determined that the amount of displacement in the flexible portion is within the range of the predetermined threshold value.

* * * * *